(12) United States Patent
Ben-Haim et al.

(10) Patent No.: US 7,310,555 B2
(45) Date of Patent: *Dec. 18, 2007

(54) REGULATION OF EXCITABLE TISSUE CONTROL OF THE HEART BASED ON PHYSIOLOGICAL INPUT

(75) Inventors: Shlomo Ben-Haim, Haifa (IL); Nissim Darvish, Haifa (IL); Itzhak Shemer, Haifa (IL); Yehuda Snir, Yokneam Illit (IL)

(73) Assignee: Impulse Dynamics N.V., Curacao (AN)

( * ) Notice: Subject to any disclaimer, the term of this patent is extended or adjusted under 35 U.S.C. 154(b) by 85 days.

This patent is subject to a terminal disclaimer.

(21) Appl. No.: 10/800,169

(22) Filed: Mar. 10, 2004

(65) Prior Publication Data

US 2004/0215267 A1 Oct. 28, 2004

Related U.S. Application Data (63) Continuation of application No. 09/831,100, filed as application No. PCT/IL99/00594 on Nov. 4, 1999, now Pat. No. 6,725,093.

(60) Provisional application No. 60/107,479, filed on Nov. 6, 1998.

(30) Foreign Application Priority Data

Nov. 16, 1998 (IL) .................................. 127092

(51) Int. Cl.
*A61N 1/362* (2006.01)
(52) U.S. Cl. ........................................................ 607/9
(58) Field of Classification Search .................... 607/9, 607/19–20
See application file for complete search history.

(56) References Cited

U.S. PATENT DOCUMENTS

| | | | |
|---|---|---|---|
| 4,554,922 A | | 11/1985 | Prystowsky |
| 4,884,576 A | * | 12/1989 | Alt .............................. 607/18 |
| 5,018,522 A | | 5/1991 | Mehra |
| 5,083,564 A | | 1/1992 | Scherlag |
| 5,205,284 A | | 4/1993 | Freeman |

(Continued)

FOREIGN PATENT DOCUMENTS

EP 0 503 839 9/1992

(Continued)

OTHER PUBLICATIONS

A.H. Foster et al., "Acute Hemodynamic Effects of Atrio-Biventricular Pacing In Humans", 1995, The Society of Thoracic Surgeons vol. 59, pp. 294-299.

(Continued)

*Primary Examiner*—Carl Layno
(74) *Attorney, Agent, or Firm*—Wolf, Block, Schorr & Solis-Cohen LLP; William H. Dippert (57) ABSTRACT

A method and apparatus (30) for modifying contractility of the heart of a patient. The method includes receiving signals from a sensor (22, 23, 46) coupled to the body of the patient indicative of physiological activity. The signals are analyzed to derive a measure of the physiological activity, and excitable tissue control (ETC) stimulation is applied to the heart (20) so as to enhance contractility of the heart muscle responsive to the measure.

18 Claims, 8 Drawing Sheets

U.S. PATENT DOCUMENTS

| | | | |
|---|---|---|---|
| 5,284,491 | A | 2/1994 | Suton et al. |
| 5,431,688 | A | 7/1995 | Freeman |
| 5,447,525 | A | 9/1995 | Powell et al. |
| 5,514,162 | A | 5/1996 | Bornzin et al. |
| 5,620,468 | A | 4/1997 | Mongeon et al. |
| 5,626,622 | A | 5/1997 | Cooper |
| 5,683,429 | A | 11/1997 | Mehra |
| 5,697,953 | A | 12/1997 | Kroll et al. |
| 5,755,740 | A | 5/1998 | Nappholz |
| 5,792,198 | A | 8/1998 | Nappholz |
| 5,800,464 | A | 9/1998 | Kieval |
| 5,807,234 | A | 9/1998 | Bui et al. |
| 5,871,506 | A | 2/1999 | Mower |
| 6,006,134 | A | 12/1999 | Hill et al. |
| 6,233,487 | B1 * | 5/2001 | Mika et al. .................... 607/27 |
| 6,292,693 | B1 * | 9/2001 | Darvish et al. ................ 607/9 |
| 6,725,093 | B1 * | 4/2004 | Ben-Haim et al. ............. 607/9 |
| 2004/0138710 | A1 * | 7/2004 | Shemer et al. ................. 607/2 |

FOREIGN PATENT DOCUMENTS

| | | |
|---|---|---|
| WO | WO 96/16696 | 6/1996 |
| WO | WO 97/25098 | 7/1997 |
| WO | WO 98/10830 | 3/1998 |
| WO | WO 98/10831 | 3/1998 |
| WO | WO 98/10832 | 3/1998 |
| WO | WO 98/19719 | 4/1998 |
| WO | WO 99/06105 | 2/1999 |
| WO | WO 00/01443 | 1/2000 |
| WO | WO 00/04947 | 2/2000 |

OTHER PUBLICATIONS

S. Cazeau et al., "Multisite Pacing For End-Stage Heart Failure: Early Experience", Pacing and Clinical Electrophysiology vol. 19, Nov. 1996, Part II, pp. 1748-1757.

Yu et al., "Does Biventricular Pacing Provide Better Cardiac Function Than . . . ?" Abstract, Heart Failure Society Abstracts-on-Disk, Sep. 13-16, 1998 Boca Raton, Florida.

A. Auricchio et al., "Acute Pacing of the Left Ventricle is Associated with Largest . . . ", Abstract, Heart Failure Society Abstracts-on-Disk, Sep. 13-16, 1998 Boca Raton, Florida.

C. Leclercq et al., "Comparative Effects of Permanent Viventricular Pacing In Class III & . . . ", Pacing and Clinical Electrophysiology, Apr. 1998, vol. 21, No. 4, Part II, p. 911.

P.F. Bakker et al., "Beneficial Effects of Biventricular Pacing of Congestive Heart Failure", PACE, vol. 17, Apr. 1994, Part II, one page.

P.F. Bakker et al., "Biventricular Pacing Improves Functional Capacity in Patients with End-Stage Congestive Heart Failure", PACE, Apr. 1995, Part II, one page.

H. Antoni et al., "Polarization Effects of Sinusoidal 50 Hz Alternating Current on Membrane Potential of Mammalian Cardiac Fibres", Pflugers Arch. 314, pp. 274-291, 1970.

Guidant Product Catalogue, 2001, 2 pages. (http://www.guidant.com/glossary.htm.).

* cited by examiner

REGULATION OF EXCITABLE TISSUE CONTROL OF THE HEART BASED ON PHYSIOLOGICAL INPUT

CROSS-REFERENCE TO RELATED APPLICATIONS

This application is a continuation patent application of U.S. patent application Ser. No. 09/831,100, filed Sep. 10, 2001 (now U.S. Pat. No. 6,725,093), which is the U.S. National Stage application of PCT Patent Application No. PCT/IL99/00594, filed Nov. 4, 1999, which claims priority from (a) U.S. Provisional Patent Application Ser. No. 60/107,479, filed Nov. 6, 1998, and (b) Israel Patent Application No. 127,092, filed Nov. 16, 1998, each of which is incorporated herein by reference.

FIELD OF THE INVENTION

The present invention relates generally to invasive devices and methods for treatment of the heart, and specifically to devices and methods for electrical stimulation of the heart muscle.

BACKGROUND OF THE INVENTION

Demand-responsive pacemakers are known in the art. Such devices provide pulses to pace the heart of a patient at a variable rate, dependent on signals received from the body of the patient.

PCT patent application PCT/IL97/00012, published as WO 97/25098, to Ben-Haim et al., whose disclosure is incorporated herein by reference, describes methods for modifying the force of contraction of at least a portion of a heart chamber by applying a non-excitatory electric field to the heart at a delay after electrical activation of the portion. The non-excitatory field is such as does not induce activation potentials in cardiac muscle cells, but rather modifies the cells' response to subsequent activation. In the context of the present patent application, the use of such a non-excitatory field is referred to as Excitable Tissue Control (ETC). The non-excitatory field may be applied in combination with a pacemaker or defibrillator, which applies an excitatory signal (i.e., pacing or defibrillation pulses) to the heart muscle.

SUMMARY OF THE INVENTION

It is an object of some aspects of the present invention to provide improved methods and apparatus for Excitable Tissue Control (ETC) of the heart so as to enhance hemodynamic performance thereof.

In preferred embodiments of the present invention, a cardiac stimulation device comprises one or more ETC electrodes, at least one sensor for sensing physiological activity, and electronic control circuitry, coupled to the ETC electrodes and sensor. The ETC electrodes and, preferably, the sensor are placed at selected sites in the heart of a patient. Alternatively, the sensor may be placed elsewhere inside or on a surface of the patient's body. The circuitry receives signals from the sensor and analyzes the signals to determine a measure of the physiological activity. Responsive to the measure, the circuitry drives the stimulation electrodes to provide ETC stimulation so as to enhance contractility of the heart muscle. Preferably, the circuitry assesses the measure so as to determine in which of a plurality of predetermined ranges the measure falls, and controls intensity of the ETC stimulation dependent on the range.

In some preferred embodiments of the present invention, the sensor comprises a heart rate sensor, and the circuitry assigns the measured heart rate to one of several heart rate ranges. Preferably, lower and upper heart rate thresholds are assigned, and the circuitry holds off the ETC stimulation when the heart rate is in a range below the lower threshold or above the upper one. When the heart rate is between the lower and upper thresholds, the circuitry preferably applies the ETC stimulation, while adjusting the intensity of the stimulation according to a predetermined function of the measured heart rate. In this manner, safety of the ETC stimulation is improved, and the intensity of the stimulation is adjusted so as to provide enhancement of the contractility, and hence of hemodynamic performance, when and as needed by the patient. Controlling the ETC stimulation by this method also reduces power consumption by the device and thus increases battery lifetime when the device is implanted in the patient's body.

In preferred embodiments of the present invention, the circuitry times the application of ETC stimulation so that the stimulation is applied at a fixed time, preferably with a predetermined delay, relative to electrical activation of the heart. The electrical activation is typically due to pacing pulses applied to the heart, but may also be due to the normal sinus rhythm, which is preferably detected by the sensor. In some preferred embodiments of the present invention, the circuitry controls the intensity of the ETC stimulation by counting heart beats in sequence and applying the stimulation only at certain of the beats in the sequence. In the context of the present patent application and in the claims, this mode of intensity control is referred to as duty cycle modulation. The inventors have found that ETC has a cumulative effect on heart muscle contractility over a period of many heart beats, and therefore it is believed that duty cycle modulation is a simple and effective means of controlling the intensity of the stimulation.

PCT patent application PCT/IL97/00235, and the corresponding U.S. patent application Ser. No. 09/254,900, which are assigned to the assignee of the present patent application and whose disclosures are incorporated herein by reference, describe a cardiac output controller using ETC stimulation. Control circuitry receives signals from one or more sensors, indicative of the heart's activity, and responsive thereto, drives the stimulation electrodes to provide the ETC stimulation to the heart. The effect of the controller on cardiac output is regulated by changing the timing of the non-excitatory stimulation pulse relative to the heart's activity, preferably relative to the heart's electrical activity or ECG signals received by the sensor (which comprises a sensing electrode). Alternatively or additionally, the controller changes other pulse characteristics, such as the voltage, current, duration, polarity, shape and frequency of the waveform, and delay of the ETC pulse relative to a pacing pulse or to sensing of an activation potential in the heart. The sensors may also include flow rate sensors, pressure sensors, temperature sensors, oxygen sensors, and other types of sensors known in the art, so as to provide additional signals indicative of hemodynamic conditions, such as cardiac output, blood pressure or blood oxygenation.

PCT patent application PCT/IL97/00236, and the corresponding U.S. patent application Ser. No. 09/254,900, which are assigned to the assignee of the present patent application and whose disclosures are incorporated herein by reference, describe a pacemaker that gives cardiac output enhancement. This pacemaker applies both excitatory (pacing) and non-excitatory (ETC) electrical stimulation pulses to the heart. By applying non-excitatory pulses of suitable strength, appropriately timed with respect to the heart's electrical activation, the contraction of selected segments of the heart muscle can be increased or decreased, thus increasing or decreasing the stroke volume of the heart.

Further aspects of ETC are described in U.S. patent application Ser. No. 09/101,723, which is similarly assigned to the assignee of the present patent application and whose disclosure is incorporated herein by reference. The application corresponds to the above-mentioned PCT patent application PCT/IL97/00012.

Israel patent application 125,424, which is assigned to the assignee of the present patent application and whose disclosure is incorporated herein by reference, describes a cardiac pacemaker that applies an extended pacing signal to the heart, thus enabling simultaneous pacing and ETC stimulation of the heart. The signal typically comprises a pacing pulse or a periodic waveform, preferably made up of a train of pulses, having an overall duration substantially longer than a pulse duration required for pacing the heart. The pacemaker is controlled to selectively apply either the extended pacing signals or ordinary, standard pacing signals, as indicated by the patient's transient and long-term hemodynamic needs.

Although preferred embodiments of the present invention are described in terms of certain specific types of sensors, typically sensing electrodes, and methods of applying and controlling the intensity of ETC stimulation, such as duty cycle modulation, the scope of the present invention is in no way limited to these modalities. It will be understood that the principles of the present invention may be applied using any other suitable types of sensors, ETC modalities and methods of controlling ETC stimulation intensity, including (but not limited to) those described in the above-mentioned PCT and Israel patent applications.

There is therefore provided, in accordance with a preferred embodiment of the present invention, a method for modifying contractility of the heart of a patient, including:

receiving signals from a sensor coupled to the body of the patient indicative of physiological activity;

analyzing the signals to derive a measure of the physiological activity;

applying excitable tissue control (ETC) stimulation to the heart so as to enhance contractility of the heart muscle responsive to the measure.

Preferably, applying the stimulation includes applying electrical signals to stimulate the heart and controlling intensity of the signals responsive to the measure, wherein controlling the intensity includes regulating a duty cycle of the signals relative to a beat rate of the heart.

Further preferably, applying the stimulation includes assessing the measure so as to determine in which of a plurality of predetermined ranges the measure falls, and varying the application of the ETC stimulation dependent on the range. Preferably, assessing the measure includes setting upper and lower thresholds with respect to the measure, and varying the application of the stimulation includes holding off the stimulation when the measure is outside a range between the thresholds.

Preferably, assessing the measure includes associating one or more of the ranges with respective types of physical activity undertaken by the patient, and wherein varying the application includes adapting the stimulation to a demand level associated with the physical activity. Most preferably, adapting the stimulation includes increasing the stimulation responsive to an increasing demand level or alternatively, decreasing the stimulation responsive to an increasing demand level.

In a preferred embodiment, analyzing the signals includes deriving a measure of hemodynamic stress.

Preferably, the measure includes a heart rate.

In another preferred embodiment, receiving the signals includes receiving a signal responsive to motion of the patient.

There is also provided, in accordance with a preferred embodiment of the present invention, apparatus for stimulating cardiac tissue in the body of a patient, including:

at least one sensor, coupled to the body which generates signals indicative of physiological activity;

one or more stimulation electrodes, which are placed in contact with the heart; and an electrical control unit, which receives and analyzes the signals from the sensor so as to derive a measure of the physiological activity and which applies an excitable tissue control (ETC) signals to the stimulation electrodes so as to enhance contractility of the heart muscle responsive to the measure.

Preferably, the at least one sensor includes an accelerometer.

Alternatively or additionally, the at least one sensor includes a sensing electrode, wherein the sensing electrode preferably includes one of the stimulation electrodes.

There is further provided, in accordance with a preferred embodiment of the present invention, a method for cardiac rehabilitation therapy, including:

receiving signals from a sensor coupled to the body of a patient indicative of physiological activity;

analyzing the signals to derive a measure of the physiological activity, the measure having a range of values;

associating the values of the measure with levels of physical activity undertaken by the patient;

applying electrical stimulation to the heart so as to induce muscular exertion thereof responsive to the level, such that over at least a part of the range, the stimulation is adjusted to reduce the muscular exertion of the heart responsive to an increase in the level of activity.

Preferably, applying the stimulation includes inducing exertion of the heart while the patient is at rest and reducing the exertion when the patient is active. Further preferably, includes applying excitable tissue control (ETC) stimulation to the heart so as to enhance contractility of the heart muscle.

The present invention will be more fully understood from the following detailed description of the preferred embodiments thereof, taken together with the drawings in which:

DETAILED DESCRIPTION OF PREFERRED EMBODIMENTS

Figure 1:
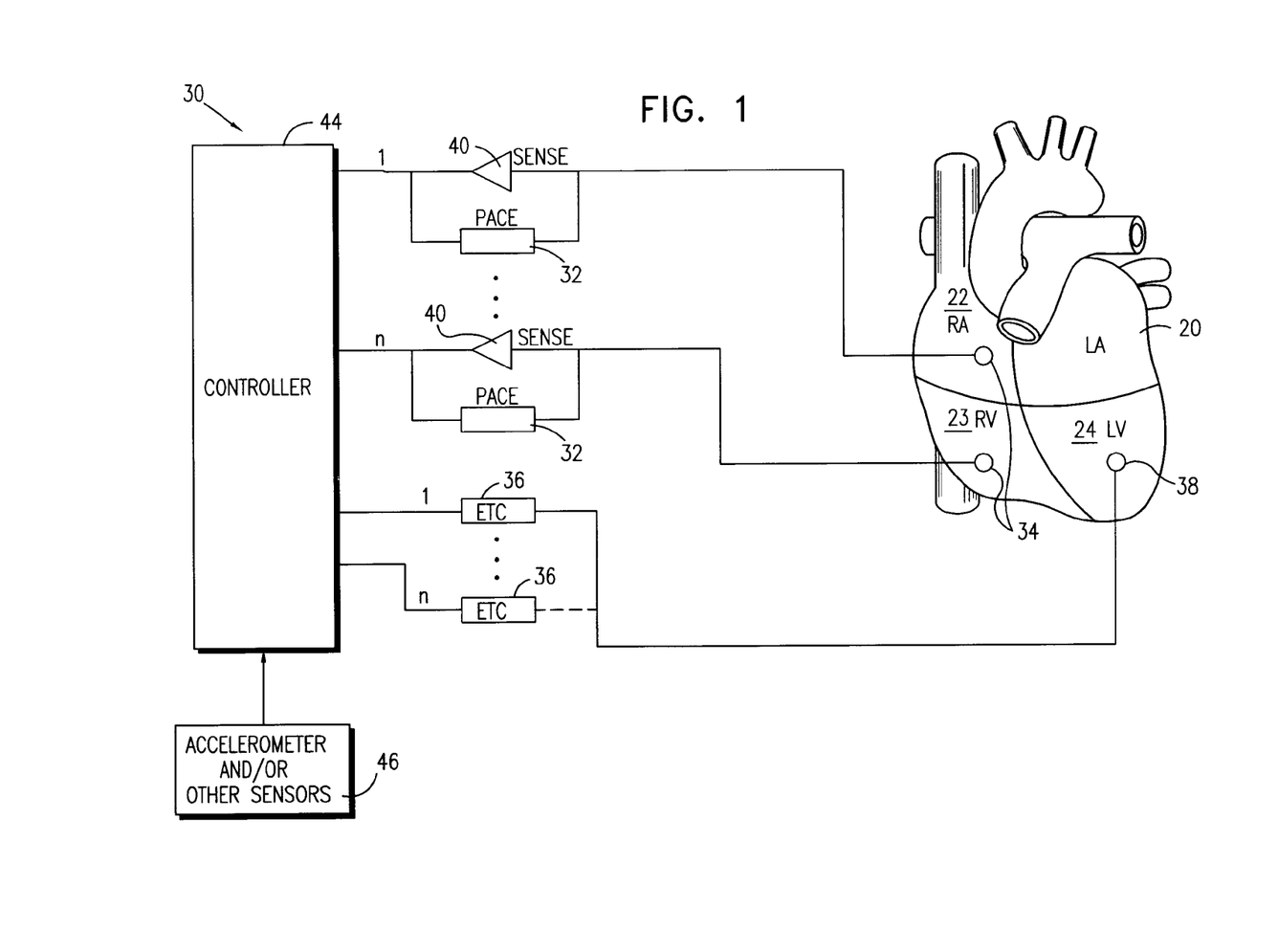
FIG. 1 is a schematic illustration of an Excitable Tissue Control (ETC) device applied to a heart, in accordance with a preferred embodiment of the present invention.

Reference is now made to FIG. 1, which is a schematic illustration showing an ETC stimulation device 30, which is applied to pace and stimulate a heart 20, in accordance with a preferred embodiment of the present invention. Details of the design and construction of devices such as device 30 are provided in the above-mentioned U.S. and PCT patent applications, as well as in the above-mentioned U.S. Provisional Patent Application No. 60/107,479.

Device 30 comprises pacing circuits 32 and ETC circuits 36, which are respectively coupled to drive one or more pacing electrodes 34 and one or more ETC electrodes 38. As shown in FIG. 1, pacing electrodes 34 are typically applied in right atrium 22 and optionally right ventricle 23, and ETC electrodes 38 are applied to left ventricle 24, most preferably epicardially or intravenously to the free wall of the left ventricle. Greater numbers of electrodes and different electrode placements are also possible.

Sensing circuits 40 receive electrogram signals from heart 20, which signals are preferably provided by the pacing and/or ETC electrodes (although separate sensing electrodes can also be used for this purpose). Control circuitry 44, preferably comprising a microprocessor and a memory, for storing programs and data. Circuitry 44 receives the signals processed by sensing circuits 40 and, based on the signals, derives the heart rate and optionally other parameters relating to cardiac function, as well. Preferably, an accelerometer or other sensor 46 provides signals to circuitry 44 responsive to motion, i.e., physical activity of the patient. Other sensors of any suitable type known in the art may also be used. Responsive to the signals from sensing circuits 40 and sensor 46, circuitry 44 controls the application of pacing and ETC stimulation to the heart, as described hereinbelow.

Figure 2A:
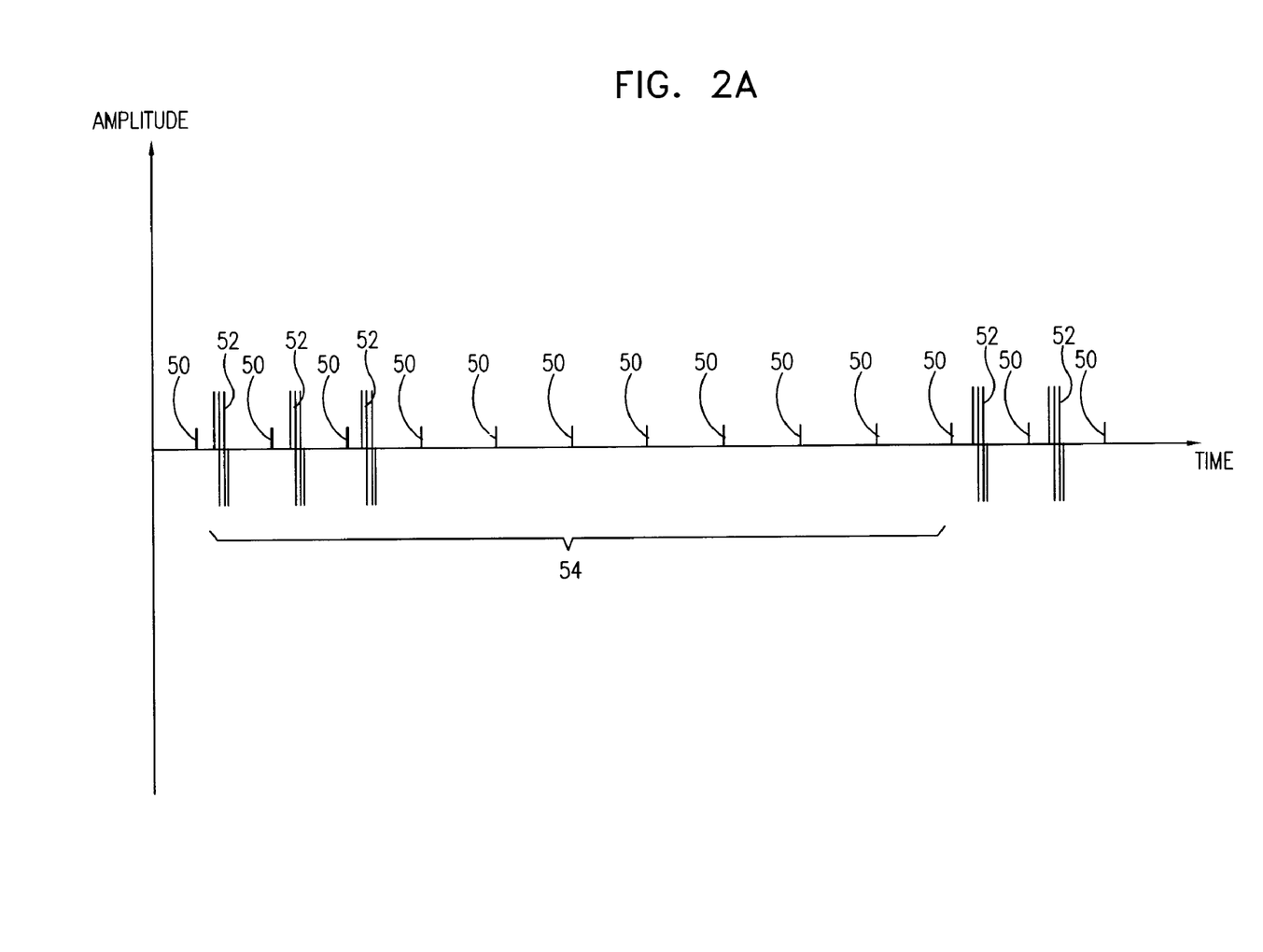
FIG. 2A is a graph that schematically shows pacing and ETC signals applied using the device of FIG. 1, in accordance with a preferred embodiment of the present invention.

FIG. 2A is a graph that schematically illustrates a sequence of pacing pulses 50 and ETC signals 52 applied by device 20, in accordance with a preferred embodiment of the present invention. The horizontal (time) axis is not drawn to scale. Over a time period 54 of about 10 sec, pacing pulses 50 are applied regularly, whereas ETC signals 52 are applied only following the first three pacing pulses during the period. This pattern of three ETC signals on, followed by seven off, is repeated in subsequent time periods, and is referred to herein as 30% duty cycle operation. The duty cycle may be varied, by decreasing or increasing the number of ETC signals in each period, between 0 and 100%. The greater the duty cycle, the more intense will be the typical effect of the ETC stimulation on cardiac contractility. Controller 44 thus instructs ETC circuit 36 to vary the duty cycle of the ETC signals so to control the ETC intensity, responsive to the sensor signals received from sensing circuit 40.

Figure 2B:
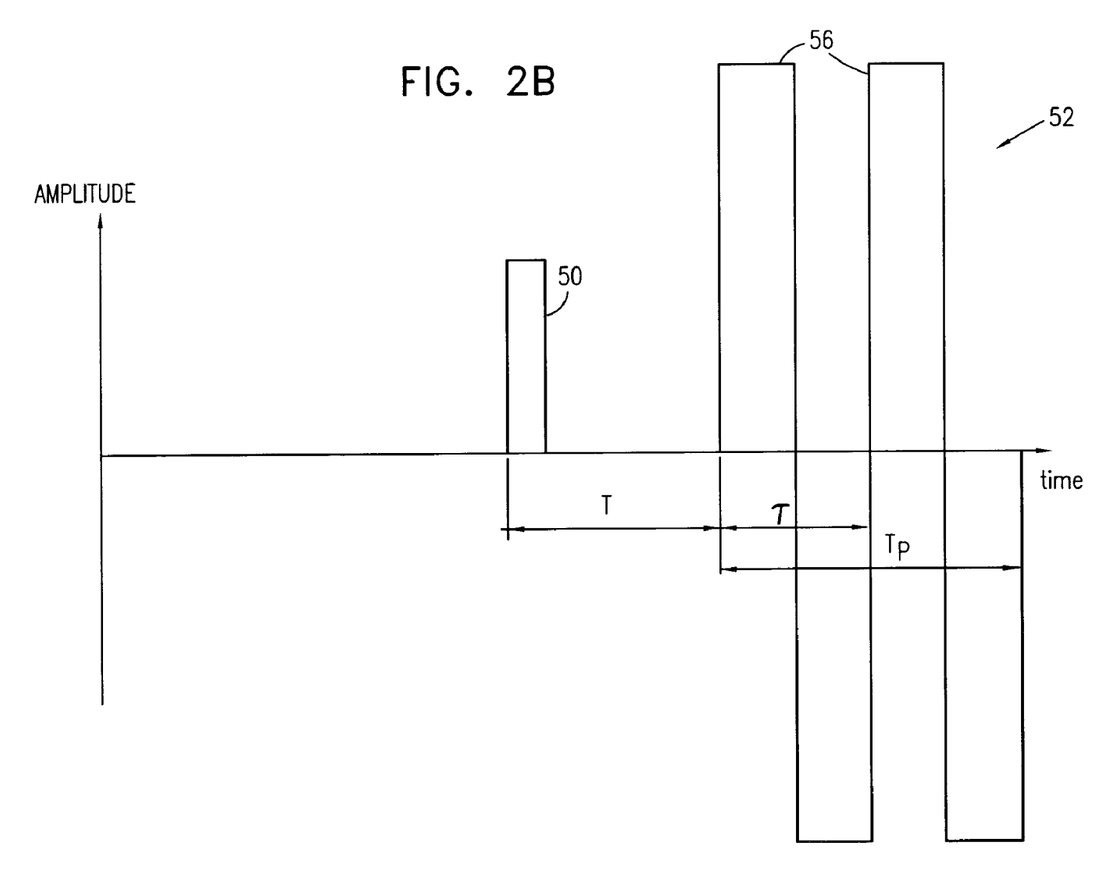
FIG. 2B is a graph showing a detail of the signals of FIG. 2A.

FIG. 2B is a graph that schematically shows a detail of pacing pulse 50 and ETC signal 52 shown in FIG. 2A. The horizontal (time) axis is not drawn to scale. Pacing pulse 50 generally comprises a standard pacing pulse of suitable amplitude, having a duration of about 2 ms or less, as is well known in the art. ETC signal 52 is preferably delayed by a time T relative to the pacing. T is chosen so that the ETC signal begins after the area of heart 20 to which electrode 38 is applied has already been electrically activated, i.e., while the heart tissue is refractory. Signal 52 preferably comprises a train of pulses 56, most preferably bipolar pulses, typically having an amplitude, a pulse period $\tau$, and a total duration $T_p$ that are substantially greater than the amplitude and duration of pacing pulse 50. Further details regarding characteristics of ETC signal 52, as well as a wide variety of other waveforms that may be used for ETC in place of signal 52, are described in the above-mentioned patent applications.

Figure 3:
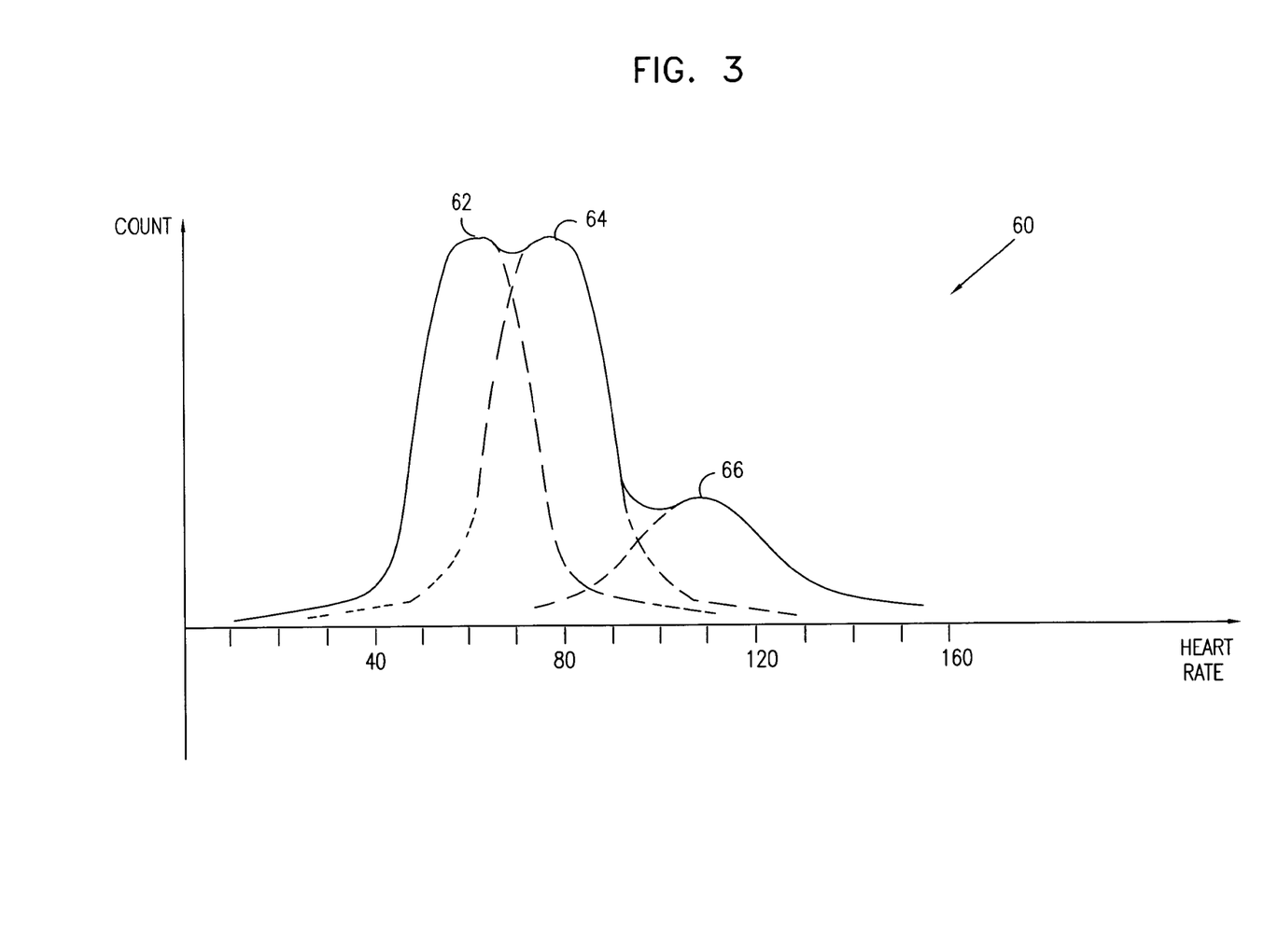
FIG. 3 is a graph showing a schematic histogram of typical heart rate measurements made over the course of a day.

FIG. 3 is a schematic histogram illustrating a distribution 60 of heart rates that would typically be measured in monitoring cardiac activity of a patient over the course of a day. The distribution could be generated by spontaneous sinus rhythm of the heart or by a demand-responsive pacemaker, as is known in the art. Distribution 60 is shown here as an aid in understanding the methods of ETC stimulation described hereinbelow, and is not meant to be an accurate representation of measurements made on a particular patient.

Distribution 60 generally comprises three major lobes, disregarding measurement artifacts falling outside the limits of the distribution. Generally, while the patient is asleep, his or her heart rate maintains a slow, steady rate falling within a lower lobe 62. During low-intensity waking activities, the heart rate rises to within a middle lobe 64. During intense activity or exertion, the heart rate is generally in upper lobe 66. Abnormalities such as arrhythmias not controlled by pacing may cause readings of fast heart rates while at rest or abnormally slow heart rates during waking activities, which fall outside their proper lobes. Such abnormalities are preferably revealed by comparing readings from accelerometer 46 (FIG. 1) to the heart rate measurements.

Figure 4:
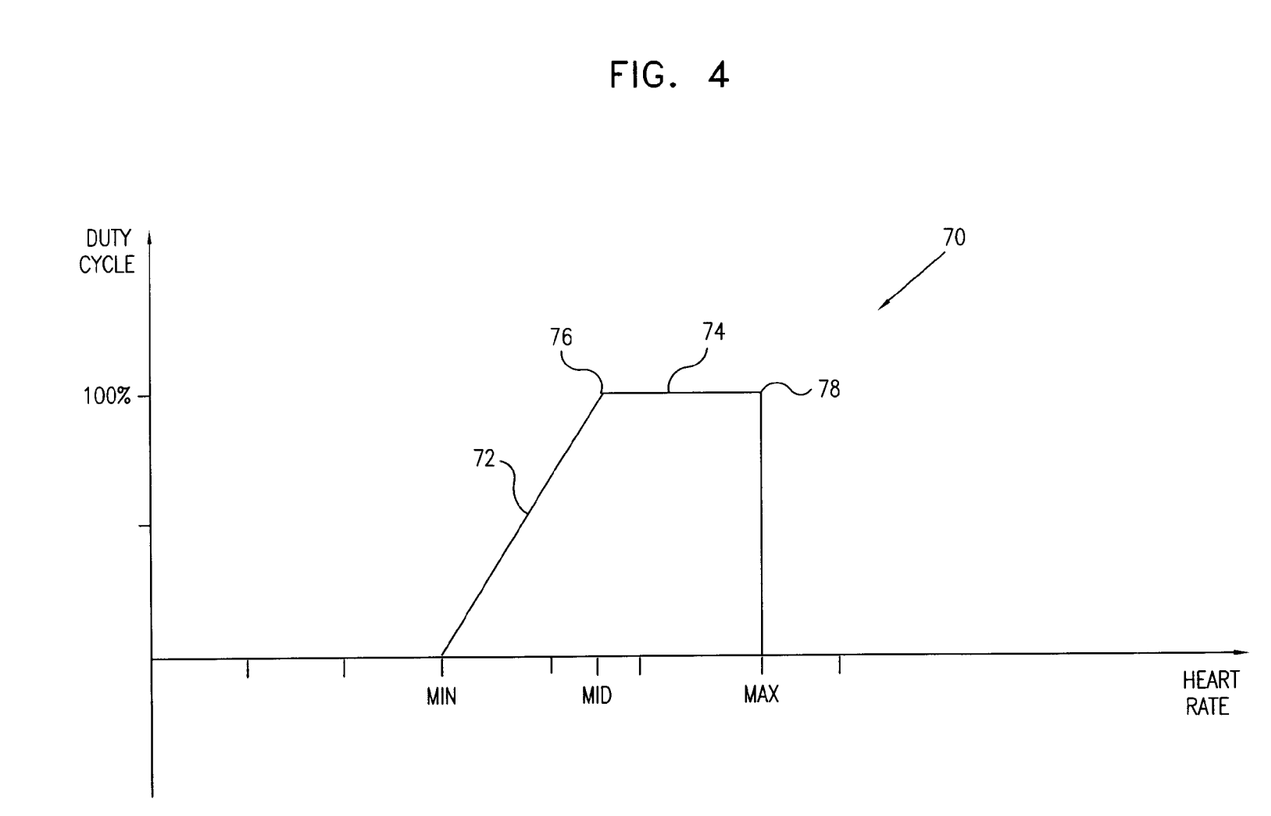
FIGS. 4-7 are graphs that schematically illustrate functions used in controlling ETC stimulation, in accordance with preferred embodiments of the present invention.

FIG. 4 is a graph that schematically illustrates a function 70 used in controlling ETC stimulation responsive to heart rate measurements, in accordance with a preferred embodiment of the present invention. The function gives the ETC duty cycle as a function of measured heart rate and is applied by device 30, or by another suitable, similar device, in generating a sequence of ETC signals such as that shown in FIG. 2A. As described hereinabove, the duty cycle of the ETC stimulation is varied between minimum and maximum values, preferably 0 and 100%, by increasing or decreasing the number of signals 52 applied by ETC circuit 36 during time period 54.

The principle exemplified by function 70 is that ETC stimulation is to be applied with greater intensity, i.e., at higher duty cycle, in proportion to the body's demand for cardiac output. Thus, below a minimum heart rate value, preferably around 60 bpm, corresponding generally to sleep and resting states of the patient, the duty cycle is held at its minimum value. No ETC stimulation is applied, since there is no need to boost the patient's cardiac output. From the minimum rate up to a middle value, preferably about 90 bpm, in a range 72 corresponding generally to low-intensity waking activities, the duty cycle increases gradually as a function of heart rate, reaching the maximum value at a knee 76. For high-demand activity, with heart rate in a range 74, ETC intensity is maintained at its maximum value. Above a maximum point 78, preferably at about 120 bpm, the ETC stimulation is cut off, since there may be a danger of placing excessive strain on the heart and, furthermore, the high heart rate may be due to tachycardia or incorrect measurements. Preferably, control circuitry 44 is programmable, so that the set points of function 70 and the maximum and minimum values of the duty cycle can be adjusted for the needs of the particular patient.

Figure 5:
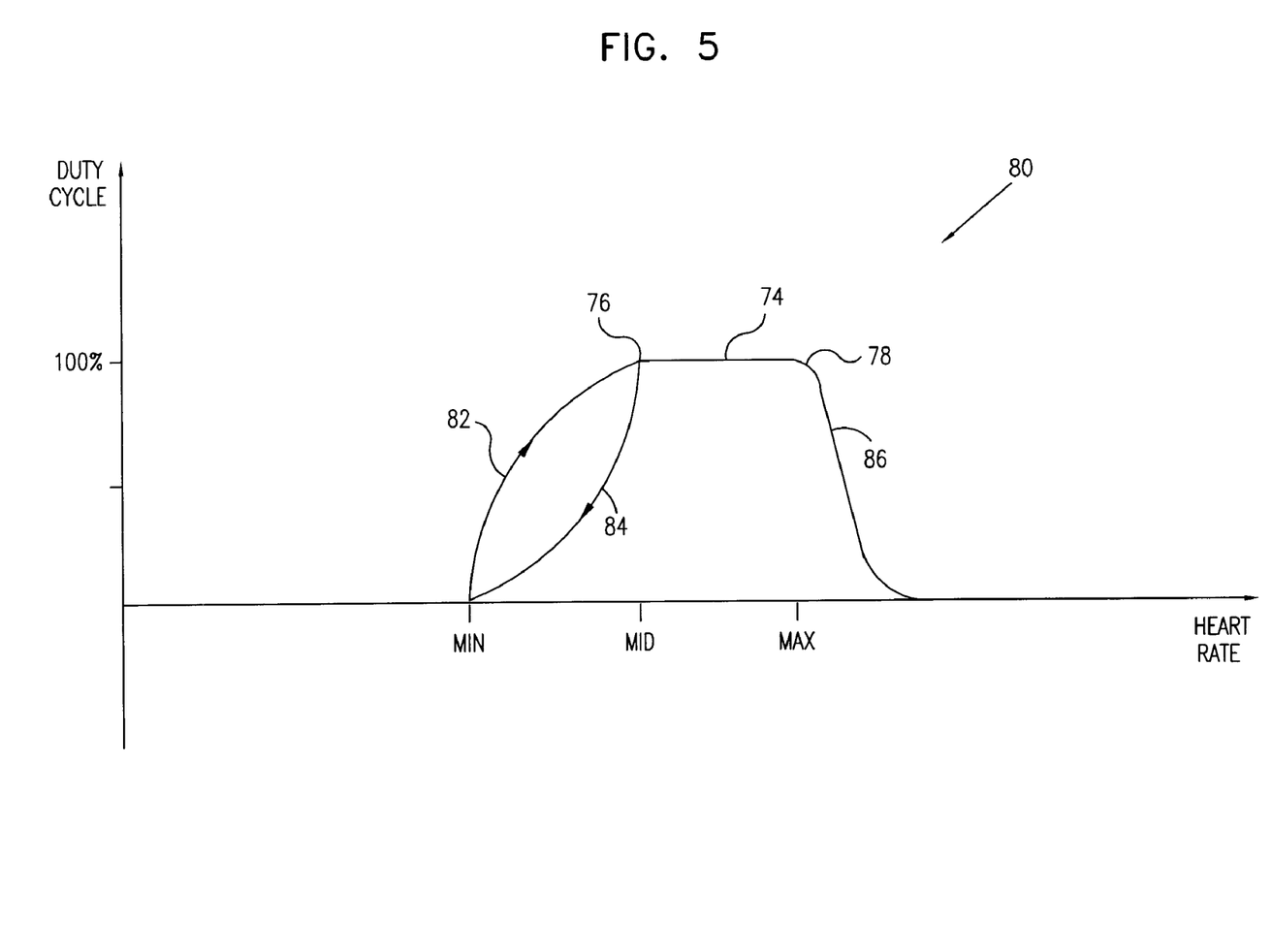

FIG. 5 is a graph that schematically illustrates another function 80 used to control ETC stimulation responsive to heart rate measurements, in accordance with an alternative preferred embodiment of the present invention. Function 80 is similar in principle to function 70, as described hereinabove, but differs in that in applying the function, control circuitry 44 takes into account not only the instantaneous measured heart rate, but also the variation of the heart rate over time. Thus, when the patient's heart rate begins to increase from the minimum toward the middle of the heart rate range, as occurs when the patient begins some strenuous activity, circuitry 44 boosts the ETC duty cycle rapidly, as indicated by a curve 82 in function 80. Because of the gradual onset of enhanced contractility when ETC stimulation is initiated, the heart's stroke volume will likewise increase gradually in parallel with the increased heart rate. Optionally, ETC stimulation intensity may be decreased more rapidly below point 76 when the heart rate is decreasing, as indicated by a curve 84. Preferably, the rates of increase and decrease of the ETC signal intensity, as functions of increasing or decreasing heart rate, are programmable, along with other signal parameters.

It is also noted that function 80 includes a gradual cutoff of ETC duty cycle over a range 86 above maximum point 78, rather than a sharp cutoff as in function 70.

Heart rate variation may also, in itself, be used as an indicator for controlling the intensity of ETC stimulation. It is known in the art that while the body is at rest, the heart rate tends to have a high degree of variability, i.e., there are relatively large changes in the instantaneous heart rate from beat to beat. On the other hand, during exertion, when the heart is under stress, the heart rate becomes nearly constant. Thus, in a preferred embodiment of the present invention not shown in the figures, the ETC duty cycle is adjusted so as to provide ETC intensity that increases as an inverse function of heart rate variability. Most preferably, such heart rate variability assessment is used in conjunction with other parameters, such as the heart rate itself and signals from accelerometer 46, in setting the ETC intensity level. Changes in blood pH and in temperature may also be measured and used by circuitry 44 in conjunction with the heart rate in assessing physiological stress, as is known in the art, and thus determining when an increase in ETC intensity will be needed.

Other parameters relating to cardiac stress may also be sensed by sensor 42 (assuming the sensor is of an appropriate type), and used by control circuitry 44 in determining the intensity of ETC stimulation to be applied. In particular, circuitry 44 may receive or derive from measured parameters an indication of cardiac ischemia, and responsive to the indication may terminate or reduce the intensity of the ETC stimulation in order to prevent infarction or undue strain on the heart muscle. Such indications of ischemia may include, for example, a shift of the ST segment in ECG or electrogram signals or a drop in blood oxygen saturation measured in the coronary sinus.

Figure 6:
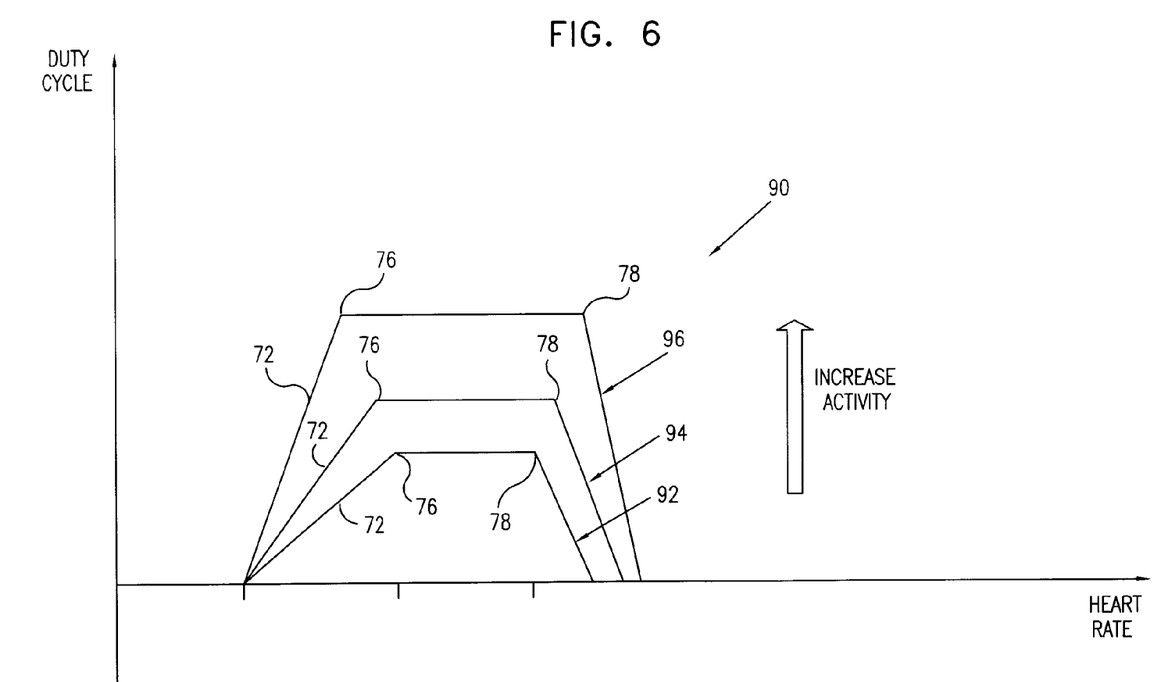

FIG. 6 is a graph that schematically illustrates a set 90 of functions 92, 94 and 96 used in controlling the intensity of ETC stimulation at various levels of patient activity, in accordance with a preferred embodiment of the present invention. Function 92 corresponds to a low activity level, such as rest, while functions 94 and 96 correspond to higher levels of activity and stress. The functions are generally similar in shape and implementation to functions 70 and 80, as described hereinabove, but are adjusted for the patient's physical activity level, preferably as measured by accelerometer 46 or other means. Generally, the functions are chosen such that the greater the patient's activity or exertion, the higher will be the intensity of ETC stimulation and the wider will be the range between points 76 and 78 over which the maximal stimulation is applied.

Using set 90, rather than a single function, is helpful in that it enables the ETC stimulation to be applied most strongly, per function 94 or 96, to meet the real need for increased cardiac output that is incurred in physical activity. The strength of stimulation is suppressed, per function 92, when physical activity is low, since under such circumstances it would appear that the increased heart rate is due to abnormalities or disease factors. Set 90 is thus useful in reducing power consumption by device 30 and minimizing unnecessary strain on the patient's heart.

Figure 7:
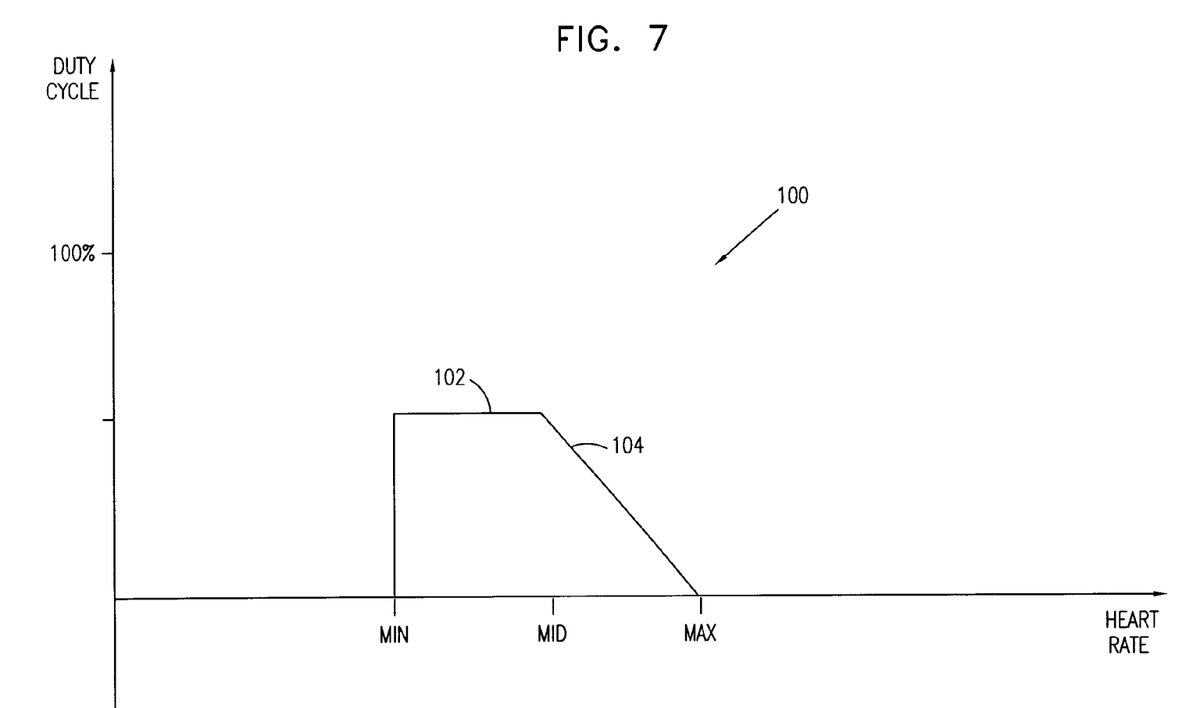

FIG. 7 is a graph that schematically illustrates another function 100, which is used, in accordance with a preferred embodiment of the present invention, to control ETC stimulation in patients suffering from serious heart disease, such as congestive heart failure (CHF). For such a patient, whose heart has been severely weakened, device 30 helps to condition and strengthen the contractility of the heart muscle, in order to alleviate the cardiac and systemic symptoms of the disease. Therefore, the objective of function 100 is not so much to provide additional cardiac output in response to physiological demand, as in the case of functions 70, 80, 92, 94 and 96, but rather to provide stimulation that will exercise the heart without causing intolerable stress to the heart muscle. Thus, when the patient's heart rate is in a low range 102 between minimal and middle values, ETC stimulation is applied at a maximal intensity, although preferably at a duty cycle that is substantially less than 100%. Above the middle value, the stimulation intensity drops off over a range 104, in response to the strain imposed by the increasing heart rate.

Preferably, circuitry 44 is programmed to operate in accordance with function 100 during an initial conditioning period after beginning treatment with device 30. Once the patient's recovery has progressed and the heart muscle has been strengthened sufficiently, circuitry 44 is reprogrammed so that it operates in accordance with a function such as function 70 or 80 or set 90.

Although in the preferred embodiments described above, the ETC intensity is controlled by varying the duty cycle of the ETC signals relative to the heart beat, it will be appreciated that many other methods can be used to control the ETC intensity, and all of these methods are within the scope of the present invention. In addition to controlling the duty cycle of ETC signals 52, other signal parameters may be controlled, including the signal amplitude, duration, delay, waveform shape and frequency, polarity, and DC offset. When multiple ETC electrodes 38 are used, the signals may also be applied to greater or lesser numbers of the electrodes and/or to electrodes located in different areas of the heart, dependent on the measurements of cardiac activity and stress.

It will thus be appreciated that the preferred embodiments described above are cited by way of example, and the full scope of the invention is limited only by the claims.

The invention claimed is:

1. A method for modifying contractility of the heart of a patient, comprising:

receiving signals from a sensor coupled to the body of the patient indicative of physiological activity;

analyzing the signals to derive a measure of the physiological activity; and applying excitable tissue control (ETC) stimulation to the heart so as to enhance contractility of the heart muscle responsive to the measure, wherein analyzing the signals comprises assessing heart rate variability of the patient, and wherein applying the ETC stimulation comprises applying the ETC stimulation responsive to the heart rate variability.

2. A method according to claim 1, wherein applying the ETC stimulation comprises increasing intensity of the ETC as an inverse function of the heart rate variability.

3. A method for modifying contractility of the heart of a patient, comprising:
- receiving signals from a sensor coupled to the body of the patient indicative of physiological activity;
- analyzing the signals to derive a measure of the physiological activity; and
- applying excitable tissue control (ETC) stimulation to the heart so as to enhance contractility of the heart muscle responsive to the measure,
- wherein applying the stimulation comprises assessing the measure so as to determine in which of a plurality of predetermined ranges the measure falls, and varying the application of the ETC stimulation dependent on the range.

4. A method according to claim 3, wherein assessing the measure comprises setting upper and lower thresholds with respect to the measure, and wherein varying the application of the stimulation comprises holding off the stimulation when the measure is outside a range between the thresholds.

5. A method according to claim 4, wherein assessing the measure comprises associating one or more of the ranges with respective types of physical activity undertaken by the patient, and wherein varying the application comprises adapting the stimulation to a demand level associated with the physical activity.

6. A method according to claim 3, wherein the measure comprises a heart rate.

7. A method according to claim 3, wherein receiving the signals comprises receiving a signal responsive to motion of the patient.

8. A method according to claim 3, wherein applying the stimulation comprises applying electrical signals to stimulate the heart and controlling intensity of the signals responsive to the measure.

9. A method according to claim 8, wherein controlling the intensity comprises regulating a duty cycle of the signals relative to a beat rate of the heart.

10. Apparatus for stimulating cardiac tissue in the body of a patient, comprising:
- at least one sensor, configured to be coupled to the body, which sensor is configured to generate signals indicative of physiological activity;
- one or more stimulation electrodes, which are configured to be placed in contact with the heart of the patient; and
- an electrical control unit, which is configured to receive and analyze the signals from the sensor so as to derive a measure of the physiological activity, and which is configured, responsive to the measure, to enhance contractility of the heart muscle by applying excitable tissue control (ETC) signals to the stimulation electrodes,
- wherein the control unit is configured to vary an intensity of the ETC signals responsive to the measure.

11. Apparatus according to claim 10, wherein the control unit is configured to vary the intensity by regulating a duty cycle of the ETC signals relative to a beat rate of the heart.

12. Apparatus for stimulating cardiac tissue in the body of a patient, comprising:
- at least one sensor, configured to be coupled to the body, which sensor is configured to generate signals indicative of physiological activity;
- one or more stimulation electrodes, which are configured to be placed in contact with the heart of the patient; and
- an electrical control unit, which is configured to receive and analyze the signals from the sensor so as to derive a measure of the physiological activity, and which is configured, responsive to the measure, to enhance contractility of the heart muscle by applying excitable tissue control (ETC) signals to the stimulation electrodes,
- wherein the control unit is configured to assign the measure to one of a plurality of predetermined ranges and to vary the application of the ETC signals dependent on the range.

13. Apparatus according to claim 12, wherein one or more of the ranges are associated with respective types of physical activity undertaken by the patient, and the control unit is configured to adapt the ETC signals to a demand level associated with the physical activity.

14. Apparatus according to claim 12, wherein the at least one sensor comprises an accelerometer.

15. Apparatus according to claim 12, wherein the at least one sensor comprises a sensing electrode.

16. Apparatus according to claim 15, wherein the sensing electrode comprises one of the stimulation electrodes.

17. Apparatus according to claim 12, wherein the measure includes heart rate variability of the patient's heart, and wherein the control unit is configured to apply the ETC signals responsive to the heart rate variability.

18. Apparatus according to claim 17, wherein the control unit is configured to increase intensity of the ETC signals as an inverse function of the heart rate variability.

* * * * *